United States Patent [19]

Mudryk et al.

[11] Patent Number: 5,847,142
[45] Date of Patent: Dec. 8, 1998

[54] PREPARATION OF NARCOTIC ANALGESICS

[75] Inventors: Bogdan Mudryk, Downingtown, Pa.; Joydeep Kant, Cherry Hill; Chester Sapino, Sewell, both of N.J.

[73] Assignee: Johnson Matthey Public Limited Company, London, England

[21] Appl. No.: 825,744

[22] Filed: Apr. 3, 1997

[30] Foreign Application Priority Data

Aug. 1, 1996 [GB] United Kingdom ............... 9616253

[51] Int. Cl.⁶ .................................................. C07D 489/02
[52] U.S. Cl. ............................................................ 546/45
[58] Field of Search .................................................. 546/45

[56] References Cited

FOREIGN PATENT DOCUMENTS 937128  9/1963  United Kingdom .

*Primary Examiner*—John M. Ford
*Attorney, Agent, or Firm*—Pillsbury Madison & Sutro LLP

[57] ABSTRACT

A novel process for preparing narcotic analgesics such as hydrocodone and hydromorphone using catalytic amounts of homogeneous organometallic complexes is disclosed.

10 Claims, No Drawings

PREPARATION OF NARCOTIC ANALGESICS

The present invention relates to a novel process for preparing narcotic analgesics such as hydrocodone and hydromorphone using catalytic amounts of homogeneous organometallic complexes.

Hydrocodone and hydromorphone are both semi-synthetic opioid analgesics with multiple actions qualitatively similar to those of codeine and morphine, involving the central nervous system and smooth muscle. The precise mechanism of action of these opiates is not known, although it is believed to relate to the existence of opiate receptors in the central nervous system.

Both hydrocodone and hydromorphone have been prepared in the past by a variety of processes including hydrogenation of codeinone (Arch. Pharm. (1920), 258, 295), oxidation of dihydrocodeine (DE 415097; U.S. Pat. No. 2,715,626), oxidation of dihydromorphine (J. Org. Chem. (1950) 15, 1103, U.S. Pat. No. 2,628,962; U.S. Pat. No. 2,654,756; U.S. Pat. No. 2,649,454), by electrolytic reduction of morphine (J. Pharm. Soc. Japan (1936), 56, 44 and (1942), 62, 347) or by catalytic rearrangement of either codeine or morphine (DE 623821, Appl. Radiat. Isot. (1987) 38, 651). However, all these processes involve a two-step process which is not cost-effective.

Catalytic rearrangement of morphine has been described using palladium black. It is not possible, however, to carry out this process on a large scale that would be suitable for manufacturing since the procedure affords 30–35% of the undesired o-desmethylthebainone along with the desired product. Isolation of the pure product is very tedious and requires extensive purification.

The present inventors have now found a new one-step route to hydrocodone and hydromorphone giving greater than 80% yield requiring minimal purification by simple methods.

Accordingly, the present invention provides a novel process for preparing a compound of formula (I)

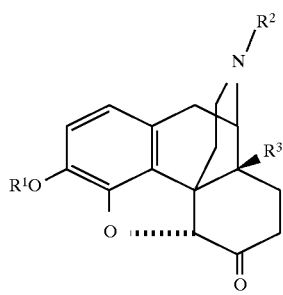

wherein $R^1$ is hydrogen, methyl or a protecting group typically used to protect phenols or alcohols; $R^2$ is hydrogen, methyl, allyl, cyclobutylmethyl, benzyl, trialkylsilyl or an amine protecting group; $R^3$ is hydrogen, hydroxyl or an amino group;

comprising reacting a compound of formula (II)

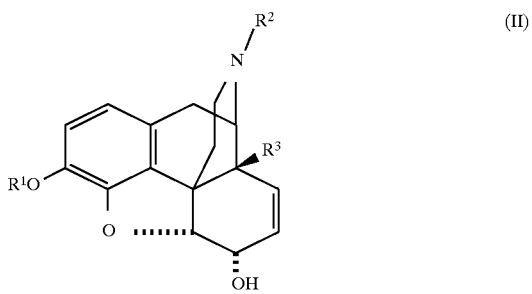

wherein $R^1$, $R^2$ and $R^3$ are as hereinbefore defined with an organometallic complex of formula (III)

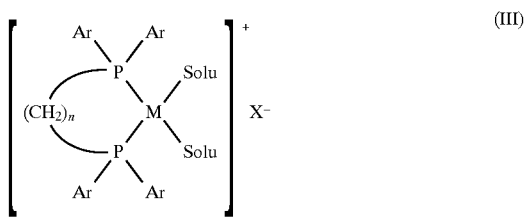

wherein M is a metal; each Ar is an aryl group, n is from 2 to 5, X is $BF_4^-$ or $ClO_4^-$ and solv is methanol, methylene chloride/methanol, tetrahydrofuran, acetone or ethanol.

Examples of alcohol or phenol protecting groups within the definition of $R^1$ include ethers (such as methoxymethyl, benzyloxymethyl, 2-(trimethylsilyl)ethoxymethyl ether, tetrahydropyranyl, phenacyl, allyl, triethylsilyl, t-butyldimethylsilyl), esters (such as acetate, pivaloate, benzoate), carbonates (such as benzyl, methyl) and sulphonates (such as methanesulphonate, toluenesulphonate).

Examples of amine protecting groups within the definition of $R^2$ include carbamates (such as methyl, 2,2,2-trichloroethyl, 2-methylsilyl, triethylsilyl, t-butyl, benzyl), amides (such as formyl, acetyl, benzoyl, cyclobutyl), sulphonates and amino acetal derivatives.

Suitably, $R^1$ is hydrogen or methyl.
Suitably, $R^2$ is hydrogen or methyl, preferably hydrogen.
Suitably, $R^3$ is hydrogen.
Suitably, M is rhodium, palladium, platinum, iridium or iron, preferably rhodium.
Suitably, Ar is a phenyl group or a cyclohexyl group. Preferably Ar is a phenyl group.
Preferably, n is 4.

The reaction is suitably carried out in a polar solvent or mixture of solvents, for example methanol, methanol/methylene chloride, tetrahydrofuran, acetone or ethanol. Preferably the reaction is carried out in a mixture of methanol/methylene chloride.

Suitably the reaction is carried out at a non-extreme temperature of from 5° C. to 50° C. Preferably the reaction is carried out at ambient temperature, for example 25° C. to 27° C.

Compounds of formula (II) are commercially available and compounds of formula (III) may be prepared by reaction of an organometallic compound with a compound of formula (IV)

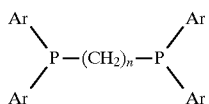

using an analogous procedure to that described in Bosnich et al, J. Am. Chem. Soc. (1991), 113, 958 and Organometallics (1988), 7, 936.

The present invention will now be described by way of example only and is not intended to be limiting thereof.

EXAMPLE 1

Large Scale Preparation of Hydrocodone

A 2 liter four-necked round-bottomed flask equipped with a mechanical stirrer, gas sparging tube, gas outlet and a thermometer was flushed with nitrogen and charged with anhydrous methanol (500ml). The solvent was de-oxygenated by bubbling nitrogen through it for 10 to 15 minutes. Bis(bicyclo[2.2.1.]hepta-2,5-diene)rhodium(I) tetrafluoroborate (1.88 g, 0.005M) and 1,4-bis (diphenylphosphino)butane (2.17 g, 0.0051M) were added under nitrogen and the solution was stirred for 30 minutes at ambient temperature. The solution was hydrogenated by sparging hydrogen gas for 30 minutes; at this point, the colour of the solution changed from orange to tan-yellow.

Excess hydrogen was removed by bubbling nitrogen through the solution for 10 minutes. Next, codeine (150 g, 0.5M) was added to the stirred solution under a stream of nitrogen. After stirring the reaction mixture for 5 to 15 minutes, hydrocodone started to precipitate out as fine crystals, methylene chloride (300 ml) was added to dissolve all the solids. The dark-red coloured homogeneous solution was stirred for 1 hour. After completion of the reaction, the solution was concentrated under vacuum at ambient temperature to about half of its original volume. The precipitated product was filtered, slurried on the filter with cold methanol (100 ml), washed with methanol (1×100 ml), and dried under vacuum for 16 hours at 60° to 70° C. to afford 124.5 g (83%) of hydrocodone as a free base.

$^1$H NMR (CDCl$_3$): δ1.26 (qd, J=4.3 Hz and 13.0 Hz, 1H); 1.75–1.90 (m, 2H); 2.06 (td, J=4.6 Hz and 12.0 Hz, 1H); 2.20 (td, J=3.4 Hz and 12.0 Hz, 1H); 2.30 (dd, J=6.0 Hz and 18.5 Hz, 1H); 2.36 (td, J=4.7 Hz and 13.7 Hz, 1H); 2.38–2.48 (m, 1H); 2.43 (s, 3H); 2.51–2.61 (m, 2H); 3.03 (d, J=18.5 Hz, 1H); 3.17 (dd, J=2.8 and 5.4 Hz, 1H); 3.91 (s, 3H); 4.65 (s, 1H); 6.63 (d, J=8.2 Hz, 1H); 6.70 (d, J=8.2 Hz, 1H).

$^{13}$C NMR (CDCl$_3$): δ19.8; 25.3; 35.3; 40.0; 42.4; 42.7; 46.58; 46.65; 56.6; 58.9; 91.2; 114.5; 119.5; 126.2; 127.2; 142.5; 145.2; 207.5.

EXAMPLE 2

Preparation of Hydromorphone

A 100 ml three-necked round-bottomed flask equipped with a magnetic stirrer, gas inlet, gas outlet and a thermometer was flushed with nitrogen and charged with anhydrous methanol (10 ml) and methylene chloride (5 ml). The solvent was de-oxygenated by bubbling dry nitrogen through it for 10 minutes. Under a stream of nitrogen, bis(bicyclo[2.2.1.]hepta-2,5-diene)rhodium(I) tetrafluoroborate (112 mg, 0.0003M) and 1,4-bis(diphenyl-phosphino)butane (130 mg, 0.00031M) were added and the orange solution was stirred for 15 minutes at ambient temperature. Next, the solution was hydrogenated by bubbling hydrogen gas for 10 minutes. Excess hydrogen was removed by bubbling nitrogen through the solution for 5 minutes. The solution of the catalyst was warmed to 40° C. and morphine (2.14 g, 0.0075M) was added under a moderate stream of nitrogen. The dark coloured solution was stirred for 4 hours at 40° C. The $^1$H NMR of the crude indicated 88% of hydromorphone, 8% of unreacted morphine and 3 to 4% of an unidentified by-product. After removal of the solvents under vacuum, the crude hydromorphone was isolated by flash chromatography (ethyl acetate/methanol 3:1) as a brown solid (1.21 g, 56%) which was purified by recrystallisation from ethanol (25 ml) to give >98% pure hydromorphone (0.75 g, 35%).

$^1$H NMR (CDCl$_3$-CD$_3$OD~10:1): δ1.25 (qd, J=4.5 Hz and 13.0 Hz, 1H); 1.79 (ddd, J=1.8, 3.4 and 12.3H, 1H); 1.88 (dq, J=4.1 and 13.0 Hz, 1H); 2.09 (td, J=4.7 Hz and 12.3 Hz, 1H) 2.25 (td, J=3.5 Hz and 12.1 Hz, 1H); 2.35 (dd, J=5.6 Hz and 18.6 Hz, 1H); 2.38–2.53 (m, 2H); 2.44 (s, 3H); 2.55–2.64 (m, 2H); 3.03 (d, J=18.6 Hz, 1H); 3.19 (dd, J=2.7 and 5.6 Hz, 1H); 4.67 (s, 1H); 6.61 (d, J=8.1 Hz, 1H); 6.70 (d, J=8.1 Hz, 1H).

$^{13}$C NMR (d6-DMSO): δ19.5; 25.0; 34.8; 39.6; 41.4; 42.5; 46.2; 46.3; 58.3; 90.3; 116.9; 119.1; 124.4; 127.3; 139.2; 143.9; 208.6.

We claim:

1. A process for preparing a compound of formula (I)

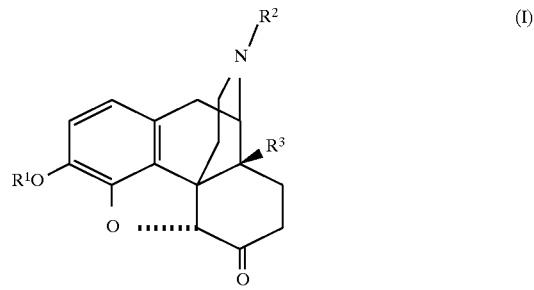

wherein $R^1$ is hydrogen, methyl or a phenol or alcohol protecting group; $R^2$ is hydrogen, methyl, allyl, cyclobutylmethyl, benzyl, trialkylsilyl or an amine protecting group; $R^3$ is hydrogen, hydroxyl or an amino group;

comprising reacting a compound of formula (II)

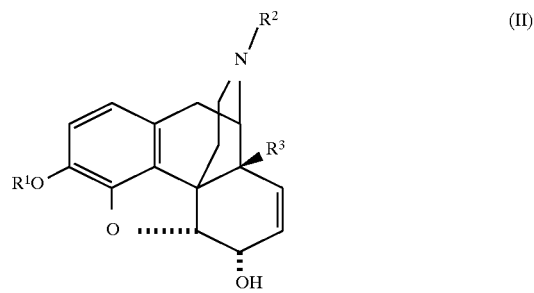

wherein $R^1$, $R^2$ and $R^3$ are as hereinbefore defined with an organometallic complex of formula (III)

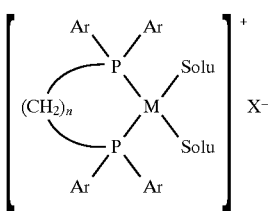 (III)

wherein M is a metal; each Ar is an aryl group; n is from 2 to 5, and X is $BF_4^-$ or $ClO_4^-$ and solv is methanol methylene chloride/methanol, tetrahydrofuran, acetone or ethanol.

2. A process according to claim 1, wherein $R^1$ is hydrogen or methyl.

3. A process according to claim 1 or 2, wherein $R^2$ is hydrogen or methyl.

4. A process according to claim 3, wherein $R^2$ is hydrogen.

5. A process according to claim 4, wherein $R^3$ is hydrogen.

6. A process according to claim 5, wherein M is rhodium, palladium, platinum, iridium or iron.

7. A process according to claim 6, wherein M is rhodium.

8. A process according to claim 7, wherein Ar is a phenyl group or cyclohexyl group.

9. A process according to claim 8, wherein Ar is a phenyl group.

10. A process according to claim 9, wherein n is 4.

* * * * *